(12) United States Patent
Mentak et al.

(10) Patent No.: US 8,048,972 B2
(45) Date of Patent: Nov. 1, 2011

(54) NANOHYBRID POLYMERS FOR OPHTHALMIC APPLICATIONS

(75) Inventors: Khalid Mentak, San Ramon, CA (US); Anthony Keslinke, Danville, CA (US); Kevin Phan, Pittsburg, CA (US)

(73) Assignee: Key Medical Technologies, Inc., San Ramon, CA (US)

( * ) Notice: Subject to any disclaimer, the term of this patent is extended or adjusted under 35 U.S.C. 154(b) by 0 days.

(21) Appl. No.: 12/823,572

(22) Filed: Jun. 25, 2010

(65) Prior Publication Data

US 2010/0261858 A1   Oct. 14, 2010

Related U.S. Application Data

(60) Continuation of application No. 11/942,527, filed on Nov. 19, 2007, now Pat. No. 7,745,555, which is a division of application No. 11/005,820, filed on Dec. 7, 2004, now Pat. No. 7,446,157.

(51) Int. Cl.
  *C08F 226/12* (2006.01)
  *C08F 26/06* (2006.01)
(52) U.S. Cl. ........... 526/88; 526/263; 526/284; 526/259
(58) Field of Classification Search .................. 526/263, 526/259, 284, 88
  See application file for complete search history.

(56) References Cited

U.S. PATENT DOCUMENTS

| | | | |
|---|---|---|---|
| 2,461,460 A | 8/1949 | Winnek |
| 2,989,529 A | 6/1961 | Schuler |
| 4,304,895 A | 12/1981 | Loshaek |
| 4,312,725 A | 1/1982 | Loshaek et al. |
| 4,390,676 A | 6/1983 | Loshaek |
| 4,528,311 A | 7/1985 | Beard |
| 4,595,548 A | 6/1986 | St. Clair et al. |
| 4,603,061 A | 7/1986 | St. Clair et al. |
| 4,611,892 A | 9/1986 | Kawashima |
| 4,636,212 A | 1/1987 | Posin |
| 4,665,123 A | 5/1987 | Goldenberg |
| 4,719,248 A | 1/1988 | Bambury |
| 4,731,079 A | 3/1988 | Stoy |
| 4,834,750 A | 5/1989 | Gupta |
| 4,851,521 A | 7/1989 | Della Valle et al. |
| 4,863,539 A | 9/1989 | Lee |
| 4,872,877 A | 10/1989 | Tiffany |
| 5,080,688 A | 1/1992 | Cohen |
| 5,093,408 A | 3/1992 | Jung |
| 5,098,445 A | 3/1992 | Hung |
| 5,132,384 A | 7/1992 | Matsuda |
| 5,194,544 A | 3/1993 | Goldberg |
| 5,217,491 A | 6/1993 | Vanderbilt |
| 5,290,892 A | 3/1994 | Namdaran |
| 5,326,506 A | 7/1994 | Vanderbilt |
| 5,331,073 A | 7/1994 | Weinschenk |
| 5,338,826 A | 8/1994 | St. Clair et al. |
| 5,359,021 A | 10/1994 | Weinschenk |
| 5,374,663 A | 12/1994 | Daicho |
| 5,403,901 A | 4/1995 | Namdaran |
| 5,428,102 A | 6/1995 | St. Clair et al. |
| 5,433,746 A | 7/1995 | Namdaran |
| 5,470,932 A | 11/1995 | Jinkerson |
| 5,480,950 A | 1/1996 | Wang |
| 5,496,368 A | 3/1996 | Wiese |
| 5,528,322 A | 6/1996 | Jinkerson |
| 5,543,504 A | 8/1996 | Jinkerson |
| 5,556,931 A | 9/1996 | Imura |
| 5,603,774 A | 2/1997 | LeBoeuf |
| 5,608,471 A | 3/1997 | Miller |
| 5,639,850 A | 6/1997 | Bryant |
| 5,654,350 A | 8/1997 | Nunez |
| 5,662,707 A | 9/1997 | Jinkerson |
| 5,674,960 A | 10/1997 | Namdaran |
| 5,693,095 A | 12/1997 | Freeman |
| 5,728,157 A | 3/1998 | Prescott |
| 5,741,883 A | 4/1998 | Bryant |
| 5,776,191 A | 7/1998 | Mazzocco |
| 5,789,463 A | 8/1998 | Odagiri |
| 5,814,680 A | 9/1998 | Imafuku |
| 5,821,306 A | 10/1998 | Hodd |
| 5,842,971 A | 12/1998 | Yoon |
| 5,849,841 A | 12/1998 | Muhlebach |
| 5,855,825 A | 1/1999 | Ito |
| 5,856,370 A | 1/1999 | Chmelir |
| 5,861,031 A | 1/1999 | Namdaran |
| 5,891,931 A | 4/1999 | LeBoeuf |

(Continued)

FOREIGN PATENT DOCUMENTS

EP   0485197   10/1996

(Continued)

OTHER PUBLICATIONS

JPO Office Action mailed on Dec. 27, 2010 for Japanese Patent App. No. 2007-545625.

(Continued)

*Primary Examiner* — Ling Choi
*Assistant Examiner* — Chun-Cheng Wang
(74) *Attorney, Agent, or Firm* — Whyte Hirschboeck Dudek S.C.; Grady J. Frenchick

(57) ABSTRACT

The present invention relates to novel materials particularly useful for ophthalmic applications and methods for making and using the same. More particularly, the present invention relates to relatively soft, optically transparent, foldable, high refractive index materials particularly suited for use in the production of intraocular lenses, contact lenses, and other ocular implants and to methods for manufacturing and using the same.

2 Claims, No Drawings

U.S. PATENT DOCUMENTS

| | | | |
|---|---|---|---|
| 5,922,550 | A | 7/1999 | Everhart |
| 5,922,821 | A | 7/1999 | LeBoeuf |
| 5,945,498 | A | 8/1999 | Hopken |
| 6,030,078 | A | 2/2000 | Ocampo |
| 6,048,951 | A | 4/2000 | Wunsch et al. |
| 6,149,692 | A | 11/2000 | Lally |
| 6,150,479 | A | 11/2000 | Klemarczyk |
| 6,201,061 | B1 | 3/2001 | Amagai |
| 6,201,089 | B1 | 3/2001 | Carter |
| 6,218,463 | B1 | 4/2001 | Molock |
| 6,265,465 | B1 | 7/2001 | Benz et al. |
| 6,271,281 | B1 | 8/2001 | Liao |
| 6,281,319 | B1 | 8/2001 | Mentak |
| 6,329,485 | B1 | 12/2001 | Vanderbilt |
| 6,342,570 | B1 | 1/2002 | Bothe et al. |
| 6,673,886 | B2 * | 1/2004 | Vanderbilt ............ 526/319 |
| 6,673,888 | B2 | 1/2004 | Kosaka |
| 7,399,811 | B2 | 7/2008 | Mentak |
| 7,446,157 | B2 | 11/2008 | Mentak |
| 7,745,555 | B2 | 6/2010 | Mentak |
| 2001/0049400 | A1 | 12/2001 | Alli |
| 2002/0037984 | A1 | 3/2002 | Vanderbilt |
| 2002/0042483 | A1 | 4/2002 | Vanderbilt |
| 2002/0042484 | A1 | 4/2002 | Vanderbilt |
| 2002/0049290 | A1 | 4/2002 | Vanderbilt |
| 2002/0064513 | A1 | 5/2002 | Maitra |
| 2002/0156047 | A1 | 10/2002 | Zhao |
| 2003/0099694 | A1 | 5/2003 | Cevc et al. |
| 2004/0063200 | A1 | 4/2004 | Chaikof et al. |
| 2004/0147501 | A1 | 7/2004 | Dolmans |
| 2004/0156880 | A1 | 8/2004 | Ravi |

FOREIGN PATENT DOCUMENTS

| | | |
|---|---|---|
| EP | 0826158 | 9/1999 |
| EP | 0820601 | 12/1999 |
| EP | 1026182 A1 | 8/2000 |
| EP | 1431350 | 6/2004 |
| GB | 2171106 | 8/1986 |
| GB | 2381482 | 5/2003 |
| JP | 2000119420 | 4/2000 |
| JP | 2005048088 | 2/2005 |
| WO | 9325593 | 12/1993 |
| WO | 9505164 | 2/1995 |
| WO | 9522991 | 8/1995 |
| WO | 9618498 | 6/1996 |
| WO | 9631791 | 10/1996 |
| WO | 9636890 | 11/1996 |
| WO | 9640303 | 12/1996 |
| WO | 9724382 | 7/1997 |
| WO | 9853920 | 12/1998 |
| WO | 9901034 | 1/1999 |
| WO | 0014591 | 3/2000 |
| WO | 0034804 | 6/2000 |
| WO | 0118078 | 3/2001 |
| WO | 0118079 | 3/2001 |
| WO | 0125301 | 4/2001 |
| WO | 0209647 | 2/2002 |
| WO | 03000777 | 1/2003 |
| WO | 2004044012 | 5/2004 |

OTHER PUBLICATIONS

English translation of examiner's comment in JPO Office Action mailed on Dec. 27, 2010 for Japanese Patent App. No. 2007-545625.
Extended European Search Report mailed Jan. 19, 2011 for European Patent App. No. 05853372.0.
Acrylens™, "A technical evaluation of foldable intraocular lenses," distributed by Ioptex Research, Inc. (1990) (Deleted from website, possibly available from web archival site.).
Acrysof® Natural single piece IOL, Product Monograph, 2004 by Alcon Laboratories, Inc.
Koch, D.D., "Alcon AcrySof Acrylic intraocular lenses," Slack Inc. (1993) 8:161-177.
Luo et al., "Modification of natural polymers: Hyaluronic acid," Methods of Tissue Engineering (Atala and Lanza eds.) (2002) Academic Press, Orlando, Florida 539-553.
Packard et al., "Poly-HEMA as a material for intraocular lens implantation: a preliminary report," J. Opthal. (1981) 65:585-587.
Prouty et al., "Fibroblast-dependent induction of a murine skin lesion with similarity to human common blue nevus," Am. J. Pathol. (1996) 148(6)L 1871-1885.
Tomihata et al., "Cross-linking of hyaluronic acid and water-soluble carbodiimide," J. Biomed. Mater. Res. (1997) 37 (2):243-251.
Wang, "Synthesis and properties of benzotriazoles as UV absorbers," J. East China Univ. of Sci. Tech. (1999) 25(2): 167-169, 173.
Website Eye Care Products pages (3) regarding Silicone SQ IOL Model 301 obtained from www.medennium.com/prod_contaract.htm, on May 2, 2005.
Website Product Description of Sensar®, obtained from www.amoinc.com/site/products/consumers on May 2, 2005.
http://www.alconlabs.com, "All about cataracts, the AcrySof IOL story," (2003) 1-3.

* cited by examiner

NANOHYBRID POLYMERS FOR OPHTHALMIC APPLICATIONS

CROSS-REFERENCE TO RELATED APPLICATIONS

This application is a continuation of U.S. patent application Ser. No. 11/942,527, filed Nov. 19, 2007, now U.S. Pat. No. 7,745,555, which is a divisional of U.S. patent application Ser. No. 11/005,820, filed Dec. 7, 2004, now U.S. Pat. No. 7,446,157, which is incorporated herein by reference. An additional sibling application Ser. No. 11/942,557, filed Nov. 19, 2007, now U.S. Pat. No. 7,399,811, which is also a divisional of parent patent application Ser. No. 11/005,820, is also incorporated by reference herein.

FIELD OF THE INVENTION

The present invention relates to novel materials particularly useful for ophthalmic applications and methods for making and using the same. More particularly, the present invention relates to relatively soft, optically transparent, foldable, high refractive index materials particularly suited for use in the production of intraocular lenses, contact lenses, and other ocular implants and to methods for manufacturing and using the same.

BACKGROUND OF THE INVENTION

Since the 1940's optical devices in the form of intraocular lenses (IOLs) have been utilized as replacements for diseased or damaged natural ocular lenses. In most cases, an intraocular lens is implanted within an eye at the time of surgically removing the diseased or damaged natural lens, such as for example, in the case of cataracts. For decades, the preferred material for fabricating such intraocular lenses was poly(methyl methacrylate), which is a rigid, glassy polymer.

Softer, more flexible IOLs have gained in popularity in recent years due to their ability to be compressed, folded, rolled or otherwise deformed. Such softer IOLs may be deformed prior to insertion thereof through an incision in the cornea of an eye. Following insertion of the IOL in an eye, the IOL returns to its original, pre-folded shape due to the memory characteristics of the soft material. Softer, more flexible IOLs as just described may be implanted into an eye through an incision that is less than 4.0 mm i.e., much smaller than the 5.5 to 8.0 mm necessary to implant more rigid IOLs. A larger incision is necessary for more rigid IOLs because the lens must be inserted through an incision in the cornea slightly larger than the diameter of the inflexible IOL optic portion. Accordingly, more rigid IOLs have become less popular in the market since larger incisions have occasionally been found to be associated with an increased incidence of postoperative complications, such as induced astigmatism.

With recent advances in small-incision cataract surgery, increased emphasis has been placed on developing soft, foldable polymer materials suitable for use in artificial IOLs. In general, these materials fall into one of three categories: hydrogels, silicones and low glass transition temperature acrylics.

In general, high water content hydrogel materials have relatively low refractive indexes, making them less desirable than other materials with respect to minimal incision size. Low refractive index materials require a thicker IOL optic portion to achieve a given refractive power. Silicone materials may have a higher refractive index than high-water content hydrogels, but tend to unfold too rapidly after being placed in the eye in a folded position. A too rapid unfolding of a folded lens can potentially damage the corneal endothelium and/or rupture the natural lens capsule and associated zonules. Low glass transition temperature acrylic materials are desirable because they typically have a high refractive index and unfold more slowly and more controllably than silicone materials when inserted into e.g., the lens capsule. Unfortunately, low glass transition temperature acrylic materials, which contain little or no water initially, may absorb pockets of water, in vivo, causing light reflections or "glistenings". Furthermore, it is difficult to achieve ideal folding and unfolding characteristics due to the temperature sensitivity of the acrylic polymers.

U.S. Pat. No. 5,480,950 issued Jan. 2, 1996 teaches of high refractive index hydrogel materials having a hydrated equilibrium water content of at least 57% for use in the manufacture of IOLs. The high refractive index hydrogel materials are cross-linked polymers prepared from mixtures of N-vinylpyrrolidone, 4-vinylpyrimidine and a vinyl pyridine having equilibrium water contents up to 90% and refractive indexes of 1.560 to 1.594 in the dry state. The IOLs as described are not implanted in a hydrated state. Rather, the IOLs are implanted in a dry, folded and elongated state and hydrated in situ. The refractive indexes in the hydrated state as used in the eye are not provided.

U.S. Patent Application Publication 2002/0049290 relates to high refractive index (RI) ophthalmic hydrogel materials U.S. Pat. No. 5,693,095 issued Dec. 2, 1997 teaches of high refractive index, low water content IOL materials. The materials taught in this particular patent are acrylic materials having an elongation of at least 150%. IOLs manufactured from a material having such elongation characteristics will not crack, tear or split when folded. However, such low water content acrylic materials have been found to be less biocompatible than other materials when manufactured into and used as IOL devices.

In the past decade, hydrophobic polymers have been used in IOL manufacturing with some success. The ophthalmic community has accepted this type of polymer as having good physical properties and acceptable biocompatibility in ocular environments. However, current IOLs made from conventional hydrophobic polymers sometimes suffer from poor optical stability in ocular fluids (e.g. glistenings, optical artifacts) and low refractive indices. The formation of unwanted particles and deposits in the bulk of hydrophobic polymers is attributed to uncontrolled water sorption and subsequent phase separation. Conventional homopolymers currently used to produce copolymers with high RIs (>1.51) absorb varying amounts of water in a sporadic fashion, creating phase separation, haze, and glistenings.

Currently, there are no foldable, high RI IOL polymers that resist the formation of glistenings and deposits.

SUMMARY OF THE INVENTION

The present invention is a new family of high RI polymers particularly suitable for, but not limited to, foldable IOL applications. Materials of this invention are optically stable in ocular fluids and resist the formation of unwanted optical artifacts. The unusual properties of the copolymers of this invention are achieved by creating nanoclusters of a generally hydrophilic polymer within a very hydrophobic polymer matrix. Water sorption is minimized and limited to the nanoclusters. In addition, the limited amount of water that is absorbed is well distributed and well dispersed within the matrix, preventing macrophase separation noted in prior art compositions. The approximate nanosize diameter of the clusters is in the range of 1.0 nm or less. Generally speaking the sizes of clusters operable in this invention will be of a diameter small enough so as to have little or interaction between visible light and the polymer network. The result is an optically clear material with stable optical properties.

This invention relates to novel copolymers for intraocular lenses ("IOL"), contact lens, and other ophthalmic and optical applications. IOLs made from the materials of this invention have a very high refractive index, and may be machined at around room temperature. IOLs of this invention may be folded and used to replace a defective natural lens of the eye by insertion through a small incision without the need for further processing or hydration. A particular advantage of the materials of this invention is their unusual hybrid character that prevents uncontrolled water sorption.

Foldable ophthalmic lens materials having controllable, uniform, relatively high water content and unexpectedly high refractive indices particularly suited for use as intraocular lenses (IOLs), or other ophthalmic devices such as but not limited to contact lenses, keratoprostheses and corneal rings or inlays, are the primary loci of the present invention.

This invention relates to copolymer compositions comprising limited amounts of a monomer having, for example, a carbazole and/or naphthyl moiety, carbazole, naphthalene, or a naphthyl group and a hydrophobic monomer. Carbazole and or naphthyl moiety monomers are added to the comonomer to increase the refractive index of the comonomer and increase the ability of the copolymer material to block blue light (wavelength up to 475 nm). A monomer having a surface tension generally in the range of 50 dyn/cm or less is used to create a very hydrophobic matrix. A hydrophilic polymer is added to create nanoclusters (in a process described below) for controlled water sorption.

Accordingly, it is an object of the present invention to provide a biocompatible IOL material having a high refractive index.

Another object of the present invention is to provide an IOL material having a high refractive index and controlled water sorption;

Still another object of the present invention is to provide an IOL material that is relatively simple to manufacture.

These and other objectives and advantages of the present invention, some of which are specifically described and others that are not, will become apparent from the detailed description and claims that follow.

DETAILED DESCRIPTION OF THE INVENTION

Materials of the present invention with high refractive indexes are desirable to allow manufacturers to manufacture thinner IOLs. A thin IOL or thin IOL optic is critical in enabling a surgeon to minimize incision size. Keeping the surgical incision size to a minimum reduces intraoperative trauma and postoperative complications. A thin IOL is also critical for accommodating certain anatomical locations in the eye such as the anterior chamber and the ciliary sulcus. IOLs may be placed in the anterior chamber for increasing visual acuity in both aphakic and phakic eyes and placed in the ciliary sulcus for increasing visual acuity in phakic eyes.

The preferred materials of the present invention have the flexibility required to allow the same to be folded or deformed so that IOLs made therefrom may be introduced into an eye through the smallest possible incision.

The novel materials of the present invention are copolymers, trimers, tetramers, etc., comprising three primary monomeric components: a high refractive index (RI) monomer, a hydrophobic monomer, and a hydrophilic monomer. A cross linker generally is included as is a UV absorber.

A high refractive index (RI) monomer of the present invention comprises a fused ring aromatic moiety coupled to an ethylenically unsaturated or vinylically unsaturated moiety. By the term "high refractive index monomer" it is intended that a polymer of the high RI monomer (i.e., a homopolymer of the monomer) has a refractive index of at least 1.50, preferably at least 1.53, and most preferably at least 1.56.

A vinylic or ethylene unsaturated moiety is, of course, well known to the art generally to mean a structure of the sort,

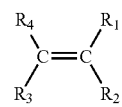

wherein:

$R_1$-$R_4$ are separately and independently, H, C, X, or $R_c$;

$R_c$ is any hydrocarbon moiety; and

X is any heteratom, providing that at least one of $R_1$-$R_4$ must be a fused ring aromatic structure or moiety as is discussed below. The fused ring aromatic structure can be, and often is, $R_c$.

"Fused ring aromatic" or polynuclear or polycyclic aromatic moieties are, of course well known. These moieties are characterized by the presence of at least two aromatic rings sharing a pair of carbon atoms. The best known examples of fused ring aromatic moieties are probably naphthalene, carbazole, anthracene, and phenanthrene. Their moieties, i.e., naphthyl, anthracyl, carbazole, and phenanthryl, are examples of preferred moieties of the high RI monomer. Further examples of such fused-ring aromatic molecules and hence their moieties include:

Fused Benzene Ring Compounds

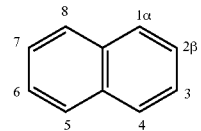

naphthalene
$C_{10}H_8$
m.p. 81° C.

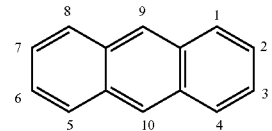

anthracene
$C_{14}H_{10}$
m.p. 217° C.

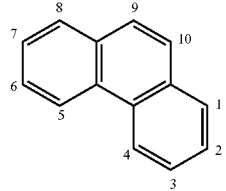

phenanthrene
$C_{14}H_{10}$
m.p. 100° C.

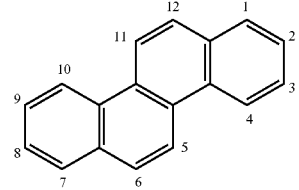

chrysene
$C_{18}H_{12}$
m.p. 253° C.

-continued

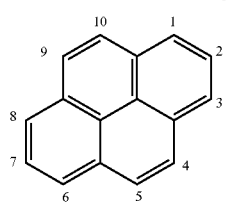

pyrene
C16H10
m.p. 150° C.

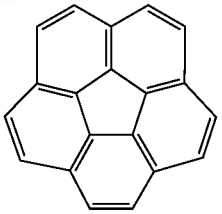

corannulene
C20H10
m.p. 268° C.

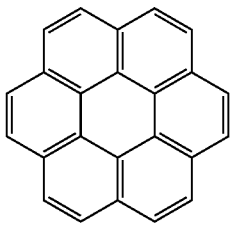

coronene
C24H12
m.p. 442° C.

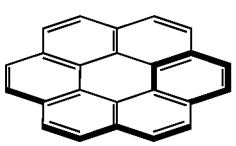

hexahelicene
C26H16
m.p. 230° C.

The above list is, of course, non-limiting. Further, the unsaturation moiety can be coupled to any one of the outer ring carbons of the above structures as would be readily apparent to one skilled in this art.

In a preferred practice, the high RI monomer comprises multimers including: a carbazole and or naphthyl moiety, the carbazole/naphthyl moiety monomer being present in the composition at a concentration of at least 15% and preferably up to about 25-45%.

The composition further includes a second monomer with a hydrophobic homopolymer, the hydrophobicity being defined as the homopolymer having a surface tension of about 50 dyn/cm or less, the second monomer being present in the copolymer, in an amount of at least about 20 weight percent, preferably about 50-60 weight percent.

The composition further includes at least about 10 weight percent of a hydrophilic monomer, preferably about 20-30 weight percent. The composition then includes a crosslinking monomer, the crosslinking monomer being present at a concentration in the range up to 10 weight percent, preferably of about 1 weight percent to about 8 weight percent.

Suitable hydrophilic monomers (i.e., monomers whose homopolymers are hydrophilic in accordance with this invention) include but are not limited to 2-hydroxy-ethylacrylate, 2-hydroxyethylmethacrylate, acrylamide, N-ornithine acrylamide, N-(2-hydroxypropyl)acrylamide, polyethyleneglycol acrylates, polyethyleneglycol methacrylates, N-vinyl pyrolidone, N-phenylacrylamide, dimethylaminopropyl methacrylamide, acrylic acid, benzylmethacrylamide, 4-hydroxybutylmethacrylate, glycerol mono methacrylate, glycerol mono acrylate, 2-sulfoethylmethacrylate, phenoxyethyl acrylate, phenoxy ethyl methacrylate, 2-(2-ethoxyethoxy) ethyl acrylate, 2-(2-ethoxyethoxy)ethyl methacrylate, furfuryl acrylate, furfuryl methacrylate, and methylthioethyl acrylamide.

Suitable hydrophobic monomers (i.e., monomers whose homopolymers are hydrophobic in accordance with this invention) include, but are not limited to, Lauryl methacrylate, lauryl acrylate, 2-ethylhexyl acrylate, 2-ethylhexyl methacrylate, n-decyl acrylate, n-decyl methacrylate, hexyl acrylate, hexyl metcarylate, stearyl acrylate, stearyl methacrylate, isodecyl acrylate, isodecyl methacrylate, isobornyl acrylate, isobornyl methacrylate, vinyl laurate, vinyl stearate, 1-hexadecyl acrylate, 1-hexadecyl methacrylate, n-myristyl acrylate, n-myristyl methacryalte, n-dodecyl methacrylamide, butyl acrylate, n-butyl methacrylate, isooctyl acrylate, isotridecyl acrylate, isooctyl methacrylate, and isotridecyl methacrylate.

Suitable crosslinkers include, for example, but are not limited to, ethylene glycol dimethacrylate (EGDMDA), diethylene glycol dimethacrylate, and triethylene glycol dimethacrylate and poly (ethylene glycol) dimethacrylate wherein ethylene glycol dimethacrylate is preferred. Suitable initiators include, for example, but are not limited to, azobis (isobutyronitrile), 2,2'-azobis(2,4-dimethylvaleronitdle), 2,2'-azobis (methylbutyronitrile), 1,1'-azobis(cyanocyclohexane), di-t-butyl peroxide, dicumyl peroxide, t-butylcumyl peroxide, 2,5-dimethyl-2,5-bis(2-ethylhexanoyl peroxy)hexane, t-butyl peroxyneodecanote, t-butyl peroxy 2-ethylhexanoate, di(4-t-butyl cyclohexyl) peroxydicarbonate, t-butyl peroxypivalate, decanoyl peroxide, lauroyl peroxide, benzoyl peroxide, 2,4-pentanedione peroxide, di(n-propyl) peroxydicarbonate, t-amyl peroxyneodecanoate and t-butyl peroxyacetate wherein 2,2'-azobis(isobutyronitrile) is preferred.

Suitable ultraviolet light absorbers include for example but are not limited to beta-(4-benzotriazoyl-3-hydroxyphenoxy) ethyl acrylate, 4-(2-acryloxyethoxy)-2-hydroxybenzophenone, 4-methacryloxy-2-hydroxybenzo-phenone, 2-(2'-methacryloxy-5'-methylphenyl)benzotriazole, 2-(2'-hydroxy-5'-methacryoxyethylphenyl)-2H-benzo-triazole, 2-[3'-tert-Butyl-2'-hydroxy-5'-(3"-methacryloyloxypropyl) phenyl]-5-chloro-benzotriazole, 2-(3'-tert-Butyl-5'(3"-dimethylvinyisilylpropoxy)-2'-hydra-xyphenyl-5-methoxybenzotriazole, 2-(3'-Allyl-2'-hydroxy-5'-methylphenyl)benzotriazole, 2-[3'-tert-Butyl-2'-hydroxy-5'-(3"methacryloyloxypropoxy)phenyl]-5-methoxybenzotriazole, and 2-[3'-tert-Butyl-2'-hydroxy-5'-(3"-methacryloyloxypropoxy)phenyl]-5-chlorobenzotriazole wherein beta-(4-benzotriazoyl-3-hydroxyphen-oxy) ethyl acrylate is the preferred ultraviolet light absorber.

A UV absorber optionally may be added to the copolymer compositions. A novel, preferred, UV/blue light absorber, i.e., vinyl anthracene, may be added to the copolymer compositions. Conventional U.V. absorbers such as a vinyl benzophenone or a vinyl benzotriazole also may be used.

A monomeric dye capable of copolymerizing with the hydrophobic and the hydrophilic monomers optionally may be added to the copolymer to attenuate specific wavelengths of light. Such dyes include but are not limited to those containing vinyl groups and are capable of absorbing violet, blue, red, and green light in the range of 400-700 nm.

Examples of such monomeric dyes include but are not limited to:
Disperse Red 13 acrylate,
Disperse Orange 3 acrylamide
Disperse Orange 3 methacrylamide
Disperse Red 1 methacrylate
Disperse Red 1 acrylate
Disperse Red 13 methacrylate
Disperse yellow 7 acrylate
Disperse yellow 7 methacrylate
Ethyl trans-α-cyano-3-indoleacrylate
[(S)-(−)-1-(4-Nitrophenyl)-2-pyrrolidinemethyl]acrylate General Preparation Steps for Polymers of Examples 1-15

The comonomers listed below were mixed in a glass flask using a magnetic stir bar for at least 30 minutes, at room temperature followed by sonication for the times indicated, and then stirring again for another 30 minutes. The combination of sonication and hydrophilic/hydrophobic repulsion forces allows the formation of nanoclusters. The size of the nanoclusters is theoretically controlled by the amount of energy provided during these steps. It was found that sonicating for about 30 minutes at a power setting of 100% on a Branson 5510 sonicator provides optically clear materials with adequate optical and physical properties. Sonicating time may vary between 1 minutes to 60 minutes depending on the formulation used. It has also been found that an optional second sonication step of at least about 10 minutes is sometimes needed to produce materials of the desired optical characteristics.

The resulting copolymers are rigid enough to be machined at around room temperature. A unique and surprising aspect of the above materials is that the refractive index of the copolymers is so high that ophthalmic lenses can be made thin enough to be folded without further processing or hydration.

Examples 1-15

|  | Monomer | Cocentration | RI | % EWC | Processing conditions |
|---|---|---|---|---|---|
| Ex. 1 | VC | 30 | 1.5690 | 1.5 | 20 minutes sonication twice |
|  | LM | 37 |  |  |  |
|  | HEMA | 30 |  |  |  |
|  | EGDM | 3 |  |  |  |
| Ex. 2 | VC | 30 | 1.5687 | 1.7 | 25 minutes sonication twice |
|  | LM | 37 |  |  |  |
|  | HEA | 30 |  |  |  |
|  | EGDM | 3 |  |  |  |
| Ex. 3 | VC | 30 | 1.5634 | 1.8 | 15 minutes sonication |
|  | EHA | 37 |  |  |  |
|  | HEMA | 30 |  |  |  |
|  | EGDM | 3 |  |  |  |
| Ex. 4 | VC | 30 | 1.5623 | 1.7 | 15 minutes sonication |
|  | EHA | 37 |  |  |  |
|  | HEA | 30 |  |  |  |
|  | EGDM | 3 |  |  |  |
| Ex. 5 | VN | 30 | 1.5541 | 1.7 | 10 minutes sonication |
|  | EHA | 37 |  |  |  |
|  | HEMA | 30 |  |  |  |
|  | EGDM | 3 |  |  |  |
| Ex. 6 | VC | 30 | 1.5512 | 1.6 | 10 minutes sonication |
|  | EHA | 37 |  |  |  |
|  | HEA | 30 |  |  |  |
|  | EGDM | 3 |  |  |  |
| Ex. 7 | VC | 25 | 1.5476 | 1.4 | 15 minutes sonication |
|  | EHA | 52 |  |  |  |
|  | HEMA | 20 |  |  |  |
|  | EGDM | 3 |  |  |  |
| Ex. 8 | VC | 25 | 1.5442 | 1.7 | 15 minutes sonication |
|  | EHA | 52 |  |  |  |
|  | HEA | 20 |  |  |  |
|  | EGDM | 3 |  |  |  |
| Ex. 9 | VC | 35 | 1.5623 | 1.7 | 10 minutes sonication |
|  | EHA | 47 |  |  |  |
|  | HEMA | 15 |  |  |  |
|  | EGDM | 3 |  |  |  |
| Ex. 10 | VC | 35 | 1.5601 | 1.1 | 15 minutes sonication twice |
|  | EHA | 47 |  |  |  |
|  | HEMA | 10 |  |  |  |
|  | EGDM | 3 |  |  |  |
| Preferred Formulations |  |  |  |  |  |
| Ex. 11 | VC | 30 | 1.5590 | 1.2 | 30 minutes sonication |
|  | EHA | 42 |  |  |  |
|  | HEMA | 25 |  |  |  |
|  | EGDM | 3 |  |  |  |
| Ex. 12 | VC | 27.5 | 1.5510 | 1.0 | 30 minutes sonication twice |
|  | LM | 44.0 |  |  |  |
|  | HEA | 25.5 |  |  |  |
|  | EGDM | 3 |  |  |  |
| Ex. 13 | VC | 27.0 | 1.5500 | 1.0 | 30 minutes sonication twice |
|  | LM | 42.0 |  |  |  |
|  | HEA | 24.0 |  |  |  |
|  | EGDM | 0.25 |  |  |  |
|  | VA | 0.45 |  |  |  |
| Ex. 14 | VC | 27.0 | 1.5511 | 1.0 | 30 minutes sonication twice |
|  | LM | 44.5 |  |  |  |
|  | HEA | 25.0 |  |  |  |
|  | EGDM | 2.5 |  |  |  |
|  | DR1 | 0.02 |  |  |  |
| Ex. 15 | VC | 27.0 | 1.5505 | 1.0 | 30 minutes sonication twice |
|  | LM | 44.5 |  |  |  |
|  | HEA | 25.0 |  |  |  |

| Monomer | Cocentration | RI | % EWC | Processing conditions |
|---------|--------------|-----|-------|----------------------|
| EGDM | 2.5 | | | |
| DR1 | 0.01 | | | |

2.5% by weight of VA and 0.3% by weight of MEB was used in all copolymer compositions.
VC: vinyl carbazole
VN: 2-vinyl naphthalene
EHA: 2-ethylhexylacrylate
LM: Lauryl methacrylate
HEMA; Hyroxyethylmethacrylate
HEA: Hydroxyethylacrylate
EGDM: ethylene glycol dimethacrylate
VA: vinyl anthracene
MEB: 2-(2'-Methacryloxy-5'methylphenyl)benzotriazole
DR 1: Disperse Red 1 Methacrylate

What is claimed is:

1. A method of making a high refractive index copolymer comprising the steps of: a) providing a composition comprising: a high refractive index monomer selected from the group consisting of vinylcarbazole, vinylnaphthalene, and mixture thereof; a hydrophobic monomer; a hydrophilic monomer; and a crosslinker; b) mixing the monomer for a time period of at least 20 minutes at about room temperature; c) sonicating the mixture of monomers for a time period of at least 10 minutes at about room temperature to produce copolymer nanoclusters in substantially hydrophobic matrix.

2. A method according to claim 1 which includes a further step of mixing the sonicated mixture for a time period of at least about 15 minutes.

* * * * *

UNITED STATES PATENT AND TRADEMARK OFFICE
CERTIFICATE OF CORRECTION

PATENT NO. : 8,048,972 B2
APPLICATION NO. : 12/823572
DATED : November 1, 2011
INVENTOR(S) : Khalid Mentak It is certified that error appears in the above-identified patent and that said Letters Patent is hereby corrected as shown below:

In the Claims:

Column 9, line 23 replace "monomer" with --monomers--

Column 10, line 19 insert --a-- after "in"

Signed and Sealed this
Eighth Day of October, 2013

Teresa Stanek Rea
*Deputy Director of the United States Patent and Trademark Office*